US00PP36549P2

(12) United States Plant Patent
Hansen

(10) Patent No.: US PP36,549 P2
(45) Date of Patent: Mar. 11, 2025

(54) ***EPIMEDIUM* PLANT NAMED 'Dream Catcher'**

(50) Latin Name: ***Epimedium* hybrid**
Varietal Denomination: Dream Catcher

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 18/831,204

(22) Filed: Sep. 13, 2024

(51) Int. Cl.
*A01H 5/02* (2018.01)
*A01H 6/00* (2018.01)

(52) U.S. Cl.
USPC ..... Plt./429

(58) Field of Classification Search
USPC ..... Plt./429
See application file for complete search history.

*Primary Examiner* — Susan McCormick Ewoldt
*Assistant Examiner* — Zachariah Allan Kay

(57) ABSTRACT

A new cultivar of *Epimedium* plant named 'Dream Catcher' characterized by its medium size habit, evergreen foliage. The flowers are light yellow spurs with reddish sepals on airy branched corymbs beginning in late spring. The foliage has three leaflets of light chartreuse with blotches of burgundy in cooler conditions and becoming deep green in summer.

2 Drawing Sheets

Botanical denomination: *Epimedium* hybrid.
Variety designation: 'Dream Catcher'.

STATEMENT REGARDING PRIOR DISCLOSURES UNDER 37 CFR 1.77(B)(6)

The Applicant asserts that no publications or advertisements relating to sales, offers for sale, or public distribution occurred more than one year prior to the effective filing date of this application. The first offer for sale was by Walters Gardens, Inc. on Sep. 15, 2023, to Pleasant Run Nursery. Subsequently, on Feb. 1, 2024, a photo and brief description of the new plant was posted on a website hosted by Walters Gardens, Inc. Walters Gardens, Inc. obtained the new plant and all information about the new plant directly from the inventor. Any information or disclosure about the claimed plant less than one year prior to the effective filing date of this application would have been obtained from directly or indirectly from the Inventor and would be a 35 U.S.C. 102(b) exception.

BACKGROUND OF THE INVENTION

The present invention relates to a new and distinct Barrenwort plant from the genus *Epimedium* and given the cultivar name 'Dream Catcher'. The new plant was the result of a single seedling selection from a cross on Apr. 30, 2014, by the inventor between 'Amber Queen' U.S. Plant Patent Nu. 17,197 as the female or seed parent and *Epimedium* x *omeiense* 'Rigoletto' (not patented) as the male or pollen parent. The seeds from the pollination were collected in May of 2014. The individually selected seedling was eventually given the breeder code 14-3-13 after being first isolated from trials at a nursery in Zeeland, MI during April of 2016. It was selected for the final introduction in April of 2019.

*Epimedium* 'Dream Catcher' has been asexually propagated at the same nursery in Zeeland, MI by division of the rhizome in 2016 and found to reproduce plants that are identical and exhibit all the characteristics of the original plant in successive generations of asexual propagation.

*Epimedium* 'Dream Catcher' has not been observed under all possible environments. The phenotype may vary slightly with different environmental conditions, such as temperature, light, fertility, moisture and maturity levels, but without any change in the genotype.

In comparison to the new plant, the female parent has smaller flowers of bright yellowish with orangish centers. The male parent has more ovate foliage with less narrow apex, the flowers are more orangish, and it is less prolific flowering.

The nearest comparison varieties known to the inventor are: 'Jester's Hat' co-pending U.S. Plant Patent Application and 'Cranberry Dancer' co-pending U.S. Plant patent application Ser. No. 18/831,203.

'Jester's Hat' has a similar habit in both height and width but has flowers with a brighter golden-yellow spurs with red sepals. 'Cranberry Dancer' has flowers with yellowish spur tips and burgundy spur bases with larger sepals of burgundy centers and white margins.

*Epimedium* 'Dream Catcher' is distinct from the parents and all other *Epimedium* known to the inventor in the following combined traits:

1. Medium-sized, dense, evergreen perennial;
2. Medium-sized flowers with light yellow spurs and reddish sepals on airy branched panicles beginning in late spring;
3. Foliage has three leaflets, light chartreuse with blotches of burgundy in cooler conditions becoming medium green in the heat of summer.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, temperature, source, and direction may cause the appearance of minor variations in color.

DETAILED PLANT DESCRIPTION

Figure 1:
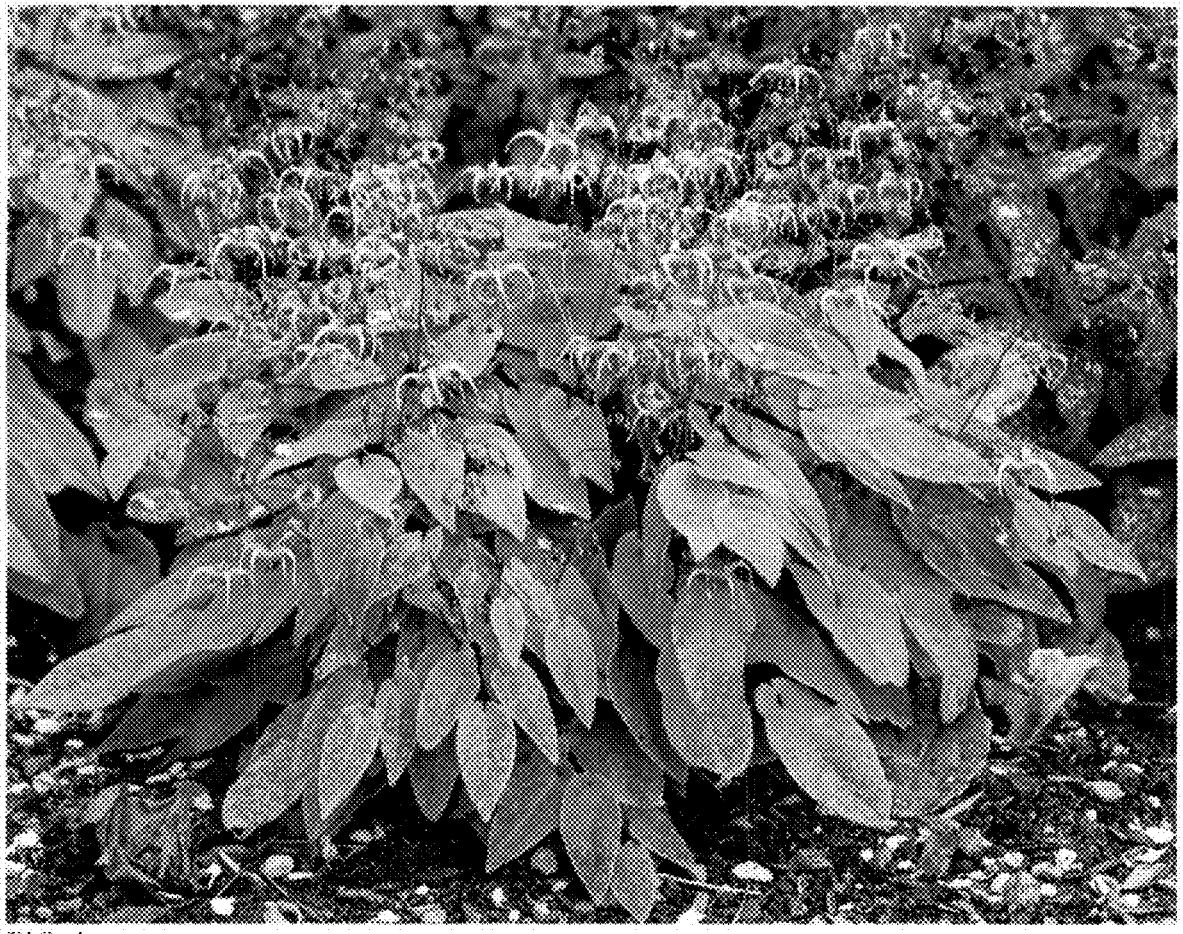
FIG. 1 shows a landscape view of a two-year-old plant in mid-season flower in an overwintered trial block at a nursery near Zeeland, Michigan.
Figure 2:
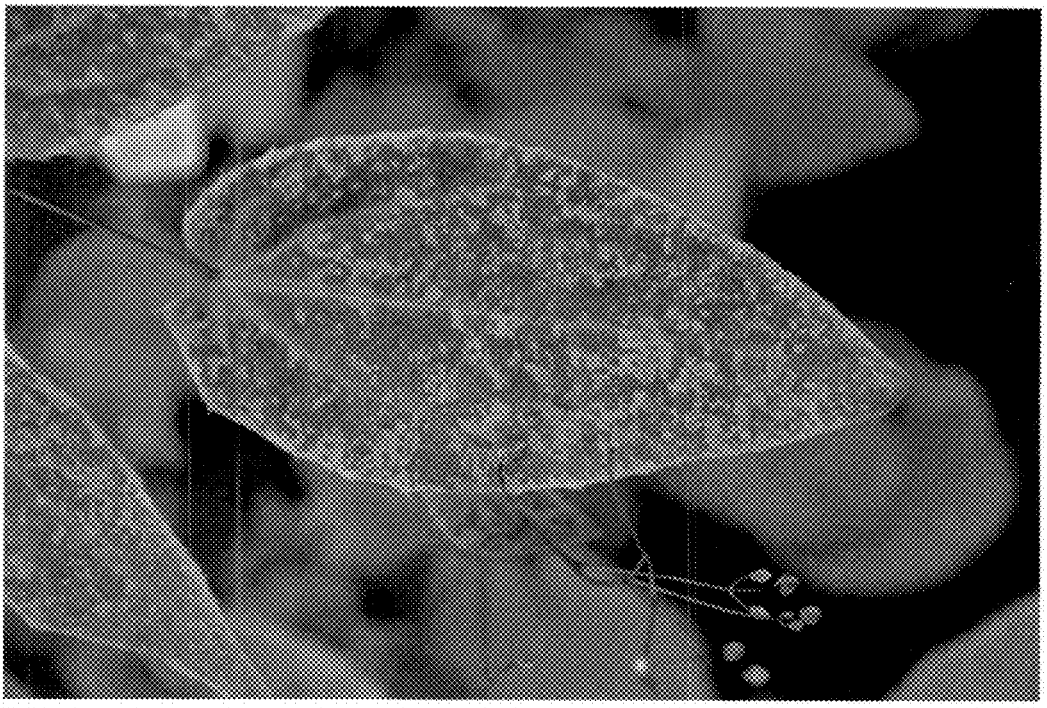
FIG. 2 shows a close-up of a leaf with burgundy blotches in early spring.
Figure 3:
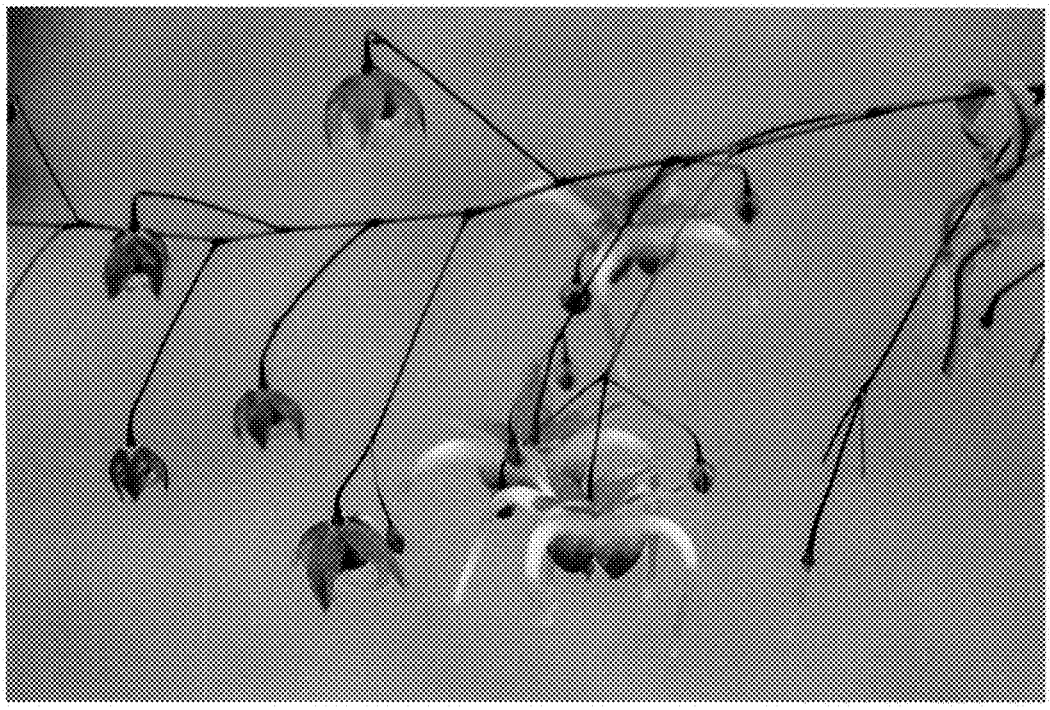
FIG. 3 shows a close-up of the scapes with flowers and buds.

The following is a detailed description of the new *Epimedium* cultivar 'Dream Catcher' based on observations of a two-year-old specimen grown in a shaded greenhouse in Zeeland, Michigan with supplemental watering and fertilizer as needed. Color descriptions are from the 2015 edition of The Royal Horticultural Society Colour Chart except where common dictionary terms are used.

Parentage: The female or seed parent is 'Amber Queen' U.S. Plant Pat. No. 17,197, the male or pollen parent is 'Rigoletto';

Propagation: Rhizome divisions;

Growth rate: Moderate;

Root development: Initiating in about 6 weeks;

Crop time: Finishing in a 3.8-liter pot from a 50 mm plug in 10 to 12 weeks;

Plant size: Soil level to top of foliar plane to about 44 cm tall and to about 90 cm wide, soil level to top of floral plane about 55 cm;

Root description: Dense, fibrous roots on rhizomes;

Rhizomes: Surface smooth, matte, glabrous; about 3.5 cm in length and 5 mm in width; color nearest RHS 164A;

Branching habit: Branches arise from rhizome;

Stem: Cylindrical; moderately glossy, glabrate beginning puberulent; strong; stiff; about 20 cm in length and 2 mm in diameter at base;

Stem color: Between RHS 174D and RHS 173D; nodes between RHS 187A and RHS 176A.

Stem aspect: Initially upright and arching with maturity;

Internode length: 20 cm;

Leaf: Typically one tri-parted leaf per node; to 21 cm wide and 17 cm long;

Leaflet: Three; oblong ovate; stiff; acute apex; cordate base slightly overlapping on center leaflet only; flat to slightly convex; finely serrulate with stiff, sharply-pointed, small spines variably in size from 1 mm to 2 mm wide and 1 mm to 2 mm in length; center leaflet to 18 cm long and 8 cm wide; side leaflets to 16 cm long and 7.5 cm wide; Leaflet surface: adaxial smooth, glabrous, moderately glossy; abaxial smooth, glabrous, matte;

Leaflet color: Young adaxial between RHS 143C and RHS 144B with irregular blotches of nearest RHS 183B, young abaxial between RHS 147C and RHS 146D; mature adaxial nearest NN137B, mature abaxial nearest N138B;

Leaflet venation: Pinnate; adaxial lightly indented; abaxial slightly costate; color adaxial between RHS 147C and RHS 146C, abaxial nearest RHS 146D;

Petioles: Arising from rhizome; cylindrical; smooth; slightly lustrous; stiff; to 20 cm long and 2 mm diameter;

Petiole color: Between RHS 174D and RHS 173D;

Petiolules: Cylindrical; smooth; slightly lustrous; stiff; to about 7.5 cm long and 1 mm diameter on center leaflets and to about 5 cm long and 0.8 mm diameter on side leaflets;

Petiolule color: Emerging foliage nearest RHS 187B maturing to between RHS 176B and RHS 177B;

Inflorescence: Compound corymb; flowering in the upper 28 cm and to about 22 cm wide; with about 24 branches, branches having to about 23 flowers; inflorescence with about 200 to 220 flowers;

Flower buds one day prior to starting to open: Globose; smooth, glabrous, about 5 mm long and 4 mm diameter;

Bud color one day prior to starting to open: Inner sepals between RHS 53A and RHS 60A, outer sepals nearest RHS 79A in longitudinal center and margins nearest RHS 76B;

Flower: Perfect; complete; actinomorphic;

Flower size: To about 20 mm in diameter and 15 mm in depth;

Flower fragrance: None detected;

Lastingness of flowers: About 7 days from initial opening dehiscence; self-cleaning;

Petals: Four; spurs; lanceolate; arcuate outwardly and curving toward center axis; apex narrowly acute; base truncate, adnate on axial portion; adaxial and abaxial smooth, glabrous and slightly lustrous; to about 11 mm long natural, 20 mm long straightened, and about 5 mm across at opening;

Petal color: When opening and fully open spur adaxial and abaxial between RHS 8C and RHS 8D with apical 2 mm nearest RHS 9A and basal 1 mm moderately blushed with nearest RHS 187B;

Pedicel: Cylindrical; puberulent to micro-glandular; to about 19 mm long and 0.3 mm diameter; average about 11 mm long and 0.3 mm diameter;

Pedicel color: Nearest RHS 178A with a slight undertone of nearest RHS 146B;

Peduncle: Cylindrical; stiff; strong; glabrous; slightly lustrous; with to about 24 branches; main peduncle aspect upright, branches outwardly to nearly 90 degrees from main axis; to about 41 cm long and 2 mm diameter at base; branches to about 12 cm long and 1 mm diameter at base;

Peduncle color: Proximal portion nearest RHS 146D moderately to heavily maculate with nearest RHS 183C, distal portion nearest RHS 146C with branch nodes between RHS 147B and RHS 147A;

Sepals: Four; rotate; single whorl; hyaline; ovate; smooth, glabrous and matte; attenuate base, acute apex; margin entire; to about 8 mm long and 5 mm across;

Sepal color: Adaxial and abaxial nearest RHS 60A;

Androecium: Four;

*Anther*.—Four; longitudinal; basifixed; extrose; oblong; to about 2.5 mm long and 1 mm across; color prior to opening nearest RHS 8B.

*Filaments*.—Four; applanate; about 3 mm long and 1 mm wide at base, narrowing distally; color proximally nearest RHS 1D, distally nearest RHS 9C.

*Pollen*.—Abundant; color nearest RHS 12B.

Gynoecium: Single; superior;

*Style*.—Cylindrical; glabrous; about 1.5 mm long and 0.3 mm diameter; color nearest RHS 145C.

*Stigma*.—Oblong; glabrous; to about 1 mm long and about 0.5 mm diameter; color nearest RHS 145C.

*Ovary*.—Oblong; glabrous; smooth; to about 2.5 mm long and 0.8 mm diameter; color nearest RHS N144D.

Fruit/seeds: None observed to date.

Resistance: Not been tested or shown to be susceptible or resistance to pests and diseases common to *Epimedium;*

Hardiness: The new plant has survived USDA winter hardiness to at least zones 5 to 8 but has not been tested yet beyond these temperatures.

It is claimed:

1. A new and distinct cultivar of *Epimedium* plant named 'Dream Catcher' as herein described and illustrated.

* * * * *